United States Patent [19]

Kasai et al.

[11] Patent Number: 4,559,304
[45] Date of Patent: Dec. 17, 1985

[54] SUBSTRATUM FOR CELL CULTURE AND A METHOD FOR CULTURING AND ISOLATING CELLS USING SAME

[75] Inventors: Shunji Kasai, Hirakata; Toshihiro Akaike, Houya; Teruo Miyata, Tokyo, all of Japan

[73] Assignee: Koken Co., Ltd., Tokyo, Japan

[21] Appl. No.: 521,083

[22] Filed: Aug. 8, 1983

[30] Foreign Application Priority Data

Aug. 9, 1982 [JP] Japan .................. 57-138153

[51] Int. Cl.$^4$ ........................... C12N 5/00; C12R 1/91
[52] U.S. Cl. ..................................... 435/240; 435/948
[58] Field of Search ............................. 435/240, 948; 260/123.7, 112 B

[56] References Cited

U.S. PATENT DOCUMENTS 4,064,007  12/1977  Choay et al. .................. 435/240
4,223,984   9/1980  Miyata et al. .................. 435/240

FOREIGN PATENT DOCUMENTS 0061549  6/1982  European Pat. Off. ............ 435/240

OTHER PUBLICATIONS

Grinnell et al., Attachment & Spreading of BHK Cells to Collagen Substrata, 1978, Proc. Nat. Acad. Sciences 75, 4408–4412.

Leighton et al., "Collagen Coated Cellulose Sponge", Science, vol. 155, pp. 1259–1261, 1967.

Hirtenstein et al., "Microcarriers for Animal Cell Culture", Third General Mtg. of ESCAT, (S. Karger ed., 1980), pp. 109–116.

Kleinman et al., "Role of Collagenous Matrices in the Adhesion and Growth of Cells", The Journal of Cell Biology, vol. 88, pp. 473–485, Mar. 1981.

*Primary Examiner*—Thomas G. Wiseman
*Assistant Examiner*—Jean A. Heck
*Attorney, Agent, or Firm*—Armstrong, Nikaido, Marmelstein & Kubovcik

[57] ABSTRACT

A substratum for cell culture which comprises a chemically modified collagen rich in either positive or negative charges when under culture conditions. The substratum is prepared by modifying the amino groups or carboxyl groups of collagen. The chemically modified collagen enhances the adherence and proliferation of animal cells much more actively than unmodified collagen in the presence or absence of bovine fetus serum. The cultured animal cells can be detached efficiently from the chemically modified collagen. This allows for highly selective isolation and recovery of the cultured animal cells which can be accomplished without incurring any injury from the chemically modified collagen.

11 Claims, 5 Drawing Figures

SUBSTRATUM FOR CELL CULTURE AND A METHOD FOR CULTURING AND ISOLATING CELLS USING SAME

BACKGROUND OF THE INVENTION

1. Field of the Invention

The present invention relates to a substratum for cell culture capable of improving and enhancing the adhesion and proliferation activities of cells to the substrate and a method for incubating and isolating the cells by using the substrate.

2. Description of the Prior Art

Collagen exists in various organs such as blood vessels, skin, liver, pancreas, kidney, as main component of the connective tissue. Collagen also functions as a supporting substance for cell growth and plays an important role as the matrix for manifestation of the functions of tissues and organs. Atelocollagen which is prepared by pepsin treatment of acid-soluble collagen or insoluble collagen has been widely used as substrate for animal cell culture. Therefore, it is clear that collagen has a superior property as the matrix of cells in vitro.

Recently, studies on the artificial organs have been developed and studies on the artificial organs incorporated with cells peculiar to each organ, that is to say, studies on the hybrid organs have been actively conducted. For instance, the development of a hybrid organ for the liver in which hepatocytes are incorporated while maintaining cell metabolic activities. In this case, it is important to adhere the cells to the substrate without losing the cell activity same as that in in vivo. The choice of the kind of the substratum used is the point of success. As the substratum for liver cells, collagen extracted from the liver is reported to be superior. (M. Rjkind et al, Connective Tissue Biomatrix: Its Isolation for Longterm Culture of Normal Rat Hepatocytes. J. Cell Biol. 87, 255 (1980)).

Also so called methods of cell technology such as cell culture and cell isolation are occupying one of the important scientific technical fields in the advancement of life science. That is to say, effective cell culture and the isolation technique of cells are the most important technique in cell technology for the production of biologically active substances derived from cells. In the culture of animal cells, it is important to select the substratum with good adhesive property of cells in order to keep the original cell activity or in order to make the cells proliferate. Also it is usually necessary to add bovine fetus serum to the culture medium in order to maintain the cell activity or to proliferate cells. However, recently, owing to the difficulties of availability and expensiveness of bovine fetus serum, the establishment of a serum free cell culture method has been earnestly desired. And recently, fibronectin which is a kind of protein has been noticed as a cell attachment factor and the cell culture in the system of fibronectin instead of bovine fetus serum has been established.

OBJECTS AND SUMMARY OF THE INVENTION

It is an object of the present invention to provide collagen substratum to which animal cells adhere effectively in the presence or absence of bovine fetus serum.

Another object of the present invention is to provide collagen substrate which makes animal cells proliferate stably and effectively.

A further object of the present invention is to provide collagen substratum capable of effectively detaching the adhered cells.

Still another object of the present invention is to provide a method for selectively isolating and recovering animal cells without cell injury.

According to the present invention, the substratum for the culture of animal cells in the presence or absence of bovine fetus serum consists of chemically modified collagen rich in negative charge or positive charge in culture conditions.

The chemically modified collagen for cell culture of the present invention enhances attachment of animal cells, for instance, mice fibroblast (L-cells) or macrophages (M$\phi$) adhere to modified collagen much better than unmodified collagen in presence or absence of bovine fetus serum and it is indicated that modified collagen is superior as the substratum for cell culture. The substratum of the present invention can be used also as the substratum of serum free culture method and therefore, the cell culture can be made at a cheaper cost, the difficulties found in case of purchasing bovine fetus serum can be avoided. Also in a system in which fibronectin is added in place of bovine fetus serum, the chemically modified collagen substratum of the present invention is far superior in attachement and proliferation of cells to results achieved with unmodified collagen substratum. Furthermore, the chemically modified collagen substratum can conduct the detachment of adhere cells at a high efficiency. Therefore, isolation and recovery of macrophages which have been desired in the fields of immunology and tumorology can be selectively made without cell injury.

DETAILED DESCRIPTION OF THE PREFERRED EMBODIMENT

Figure 1:
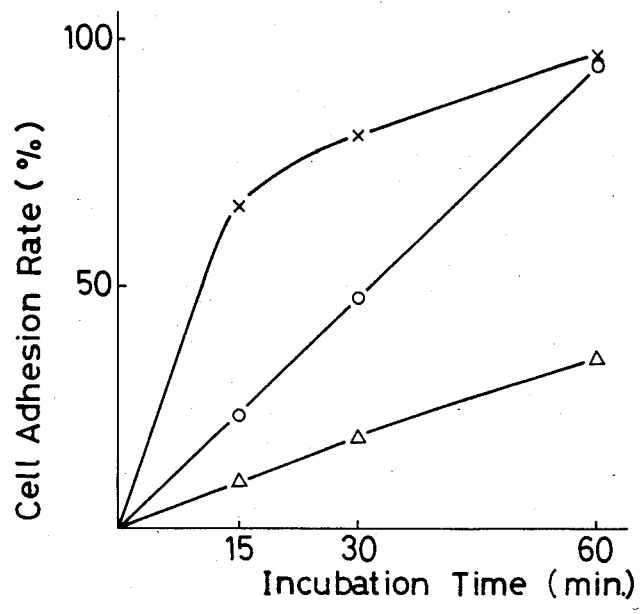
FIG. 1 is a graph showing the relation between the incubation time and cell adhesion rate of mice fibroblast (L-cells) by using various collagen substrata in the presence of bovine fetus serum.

Native collagen (unmodified collagen) bears positive charge and negative charge in the side groups of polypeptide chains. Basic amino acids orginine, lysine and histidine provide positive charges and acidec amino acids, glutamic acid and aspartic acid provide negative charges. The numbers of basic and acidic amino acid of unmodified collagen are 85 and 78 respectively per 1000 residues of amino acids, therefore there is a surplus of 7 basic amino acids.

One of the methods for obtaining collagen rich in negative charges of the present invention, is the succinylation of collagen. As shown in the following reaction formula (1), this reaction is carried out by introducing a succinyl group to the $\epsilon$-amino group of collagen with succinic anhydride to convert the amino group to a carboxyl group.

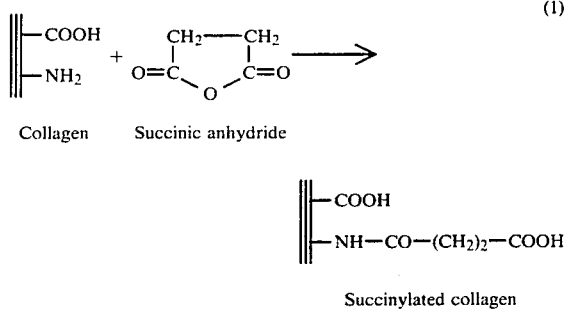

Collagen   Succinic anhydride

Succinylated collagen

By this reaction, the succinylated collagen becomes rich in negative charge. When the succinylation reaction has proceeded enough, the thus formed succinylated collagen has negative charges of 49/(1,000 residues) in excess at pH7.

It is preferable to succinylate more than 20% of all amino groups of collagen, and it is further preferable to succinylate more than 40% of all amino groups. In the case that the succinylation is too small, the adhering property of cells cannot be improved enough.

As another method for obtaining collagen rich in negative charge of the present invention, carbamylation, trifluroacetylation, trinitrobenzoylation reactions may be cited as the method to convert the amino groups to neutral derivatives, and a method of using anhydrous maleic acid may be cited as the method to convert amino groups to carboxyl group.

As the method for obtaining collagen rich in positive charge, there is an esterification method by reacting carboxyl group with alcohol in the presence of acid catalyst. This reaction is represented by the following reaction formula (2),

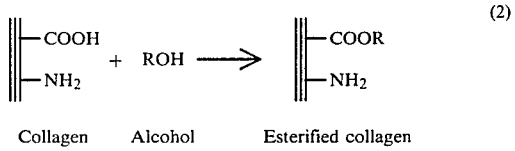

Collagen   Alcohol   Esterified collagen

In the formula (2), R represents a straight or branched aliphatic hydrocarbyl residue, preferably, methyl group, ethyl group etc. When the esterification reaction has proceeded enough, negative charges are eliminated, and therefore, the positive charges of esterified collagen are in excess by 85/(1,000 residues) at pH7. It is preferable to esterify more than 20% of all carboxyl groups of collagen, and it is further preferable to esterify more than 40%. In the case that the esterification degree is too small, the effect to enhance cell attachment cannot be obtained.

As another method for obtaining the chemically modified collagen rich in positive charges, there is a method to esterify carboxyl groups by coupling with nucleophilic groups via water-soluble carbodiimide. As a method to modify the positive charge to the side chain of arginine, there are some methods to react with butandione, 2,4-cyclohexadione, phenylglyoxal etc.

As a collagen material to be modified, atelocollagen which is prepared by solubilizing the insoluble collagen of bovine corium with pepsin may be used preferably, but acid-soluble collagen which can be extracted with only acid and insoluble collagen can be used too.

The animal cells which are incubated after adhering to the chemically modified collagen substratum of the present invention can be isolated and recovered. For instance, in the case of isolating only macrophages from a mixed system of lymphocyte and macrophage only macrophage adheres selectively to the chemically modified collagen substratum by incubating in the of presence of bovine fetus serum or fibronectin. Macrophage selectively adhered can be released and recovered at a high yield, by treating with bivalent cation chelating agent such as EDTA or EGTA without cell injury. By this method marcophage is highly selectively isolated and recovered from the above mixed system. When unmodified collagen is used as a substrata it is impossible to isolate and recover macrophage because macrophage does not efficiently adhere to unmodified collagen. Further when bovine fetus serum or fibronectin, are not present it is difficult to detach macrophage even though the adhered macrophage is treated with bi-valent cation chelating agent. Accordingly, the highly selective isolation of macrophage can be attained by using the chemically modified collagen substratum rich in negative charge or positive charge preferably in the presence of bovine fetus serum or fibronectin, and by treating the adhered macropharge with bi-valent cation chelating agent.

EXAMPLE 1

Calf skin corium was crushed and was washed in each of 5% sodium chloride and 1% sodium bicarbonate solution to remove soluble materials. After it was washed with water, pepsin was added at a ratio of 0.5% of dried collagen to skin corium suspension (pH 3.0) acidified with hydrochloric acid and insoluble collagen was dissolved at a temperature between 20° C. and 25° C. with stirring. After dissolving it, the solution was filtered successively through filter paper and millipore filter in 1 μm, 0.45 μm, and was allowed to stand overnight after adjusting the pH to 11.0 for the inactivation of pepsin. Then, the pH of the solution was adjusted to 7.0–7.5 and thus formed precipitates of atelocollagen were collected by centrifuging and were washed in water. These precipitates were dissolved in dilute hydrochloric acid of pH 3 again, and after that, were reprecipitated at pH 7.0–7.5 and were collected by centrifuging.

10 g (dry weight) of atelocollagen was dispersed in 21 of a borax buffer solution pH 10.0 and was succinylated by slowly adding 5% succinic anhydride solution in acetone. During the reaction, 1N-sodium hydroxide solution was dropped to keep the pH 10. Along proceeding of the reaction, atelocollagen precipitate dispersed in the solution was dissolved. After completing the addition of anhydrous succinic acid, the pH of the solution was adjusted to pH 4.5 to precipitate succinylated collagen. The precipitate was collected by centrifuge and washed in water and was redissolved with dilute hydrochloric acid, pH 3, and reprecipitated at pH 4.5 again and after washing in water, purified succinylated atelocollagen was obtained. The succinylation value of this succinylated atelocollagen was 80–90%.

While, 10 g of atelocollagen which was dried enough over silica gel under vacuum was immersed in anhydrous methanol containing 0.1N-hydrochloric acid for 1 week methylated atelocollagen was formed. The methyl esterification value of methylated atelocollagen was 60–80%.

Succinylated atelocolagen, methylated atelocollagen and non-modified atelocollagen were dissolved with dilute hydrochloric acid of pH 3 to make 0.3% solution and the solution was filtered through 0.45 μm millipore filter to remove bacteria. To each petri dish made of plastic for culture, each collagen solution, from which bacteria were removed, was coated, and after drying by air aseptically, these were irradiated by ultra violet ray for 1 hour to crosslink collagen. Furthermore, the collagen coated petri dishes were washed with Hank's salt solution three times.

$2.5 \times 10^4$ cells of mice fibroblast (L-cells) were seeded per each dish for culture and were incubated culture medium, Eagle culture medium containing 10% bovine fetus serum and Eagle culture medium not containing said serum were used as a culture medium. The incubation was carried out at 37° C. under 5% $CO_2$ gaseous phase. After incubating for a certain hour, the culture liquid was discarded and the cells were washed in the same culture medium three times, and the cells detached from collagen substratum were washed out. The numbers of cells adhered to the substratum were calculated by counting the numbers of the cells washed out.

Figure 2:
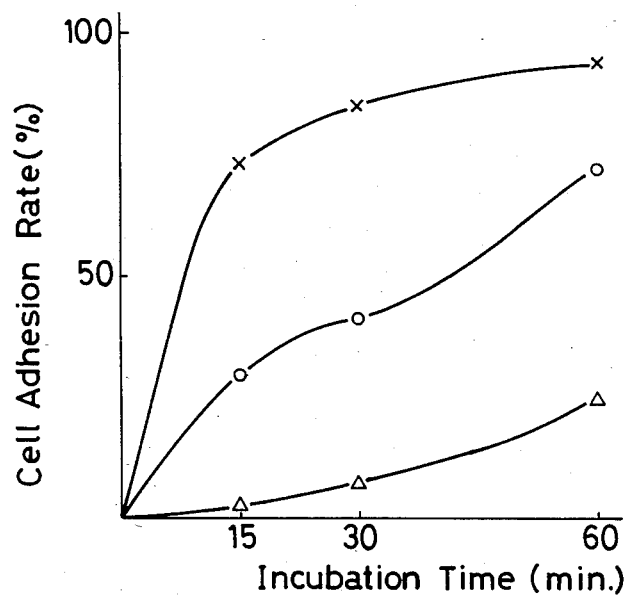
FIG. 2 is a graph showing the similar relation to those of FIG. 1 in the absence of bovine fetus serum.

The relations of incubation time with the adhesion rate of cells were shown in FIG. 1 and FIG. 2. FIG. 1 shows the result in the presence of bovine fetus serum and FIG. 2 shows the result in the absence of bovine fetus serum. And in FIG. 1 and FIG. 2, the mark Δ shows the result obtained from unmodified atelocollagen, the mark 0 shows the result obtained from succinylated atelocollagen the mark X shows the result obtained from methylated atelocollagen.

As it is clear from FIG. 1 and FIG. 2, methyl-esterified atelocollagen and succinylated atelocollagen adhered to L-cells at a higher rate than unmodified atelocollagen (control) in the presence and absence of bovine fetus serum.

EXAMPLE 2

The proliferation test of L-cells was conducted in the presence and absence of fibronectin by using culture dish coated with succinylated atelocollagen, methylated atelocollagen, unmodified atelocollagen which had been prepared by the method mentioned by Example 1. To the culture dish coated with collagens, 0.5 ml of Hank's salt solution containing 100 μg/ml of human plasma fibronectin was added, and after allowing it to stand at 4° C. overnight and washing with Hank's salt solution twice, fibronectin was fixed to collagen substratum.

Figure 3:
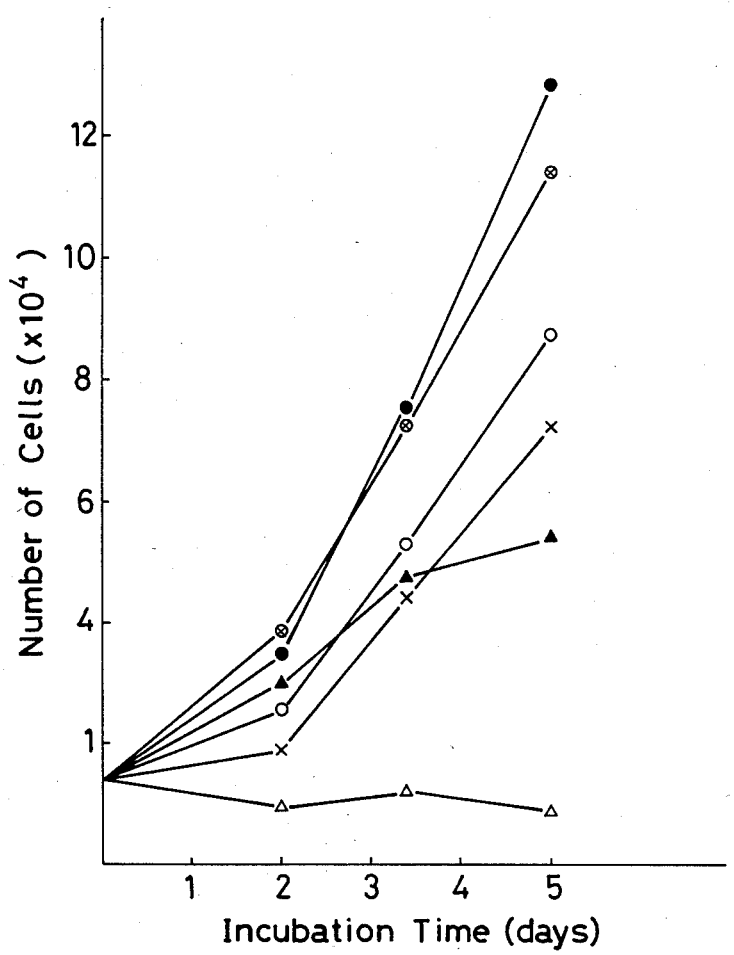
FIG. 3 is a graph showing the relation between the incubation time and the number of cells of mice fibroblast (L-cells).

$1.5 \times 10^4$ cells of L-cells per each culture dish were incubated by using serum free Eagle culture medium, and the relation of the incubation time with the numbers of the cells was tested. And the relation of the incubation time with the numbers of the cells was similarly tested on the collagen not fixed with fibronectin as a control. These results were shown in FIG. 3. In FIG. 3, the marks ▲, ● and ⊗ represent the results obtained by unmodified atelocollagen fixed with fibronectin, succinylated atelocollagen fixed with fibronectin and methylated atelocollagen fixed with fibronectin, respectively. Further, the marks Δ, o and x represent the results obtained by unmodified atelocollagen, succinylated atelocollagen and methylated atelocollagen, respectively, each of which is not fixed with fibronectin.

As seen in FIG. 3, the proliferation of L-cells was better in succinylated or methylated atelocollagen substratum than unmodified atelocollagen in both media, with and without fibronectin. Especially, it was suggested that L-cells were proliferated very well on the chemically modified atelocollagen substrata in the medium containing fibronectin.

EXAMPLE 3

The adhesiveness of macrophage to the substratum was tested by using the culture dishes coated with succinylated atelocollagen, methylated atelocollagen and unmodified atelocollagen, respectively. The exudate of mice abdomen was taken and the cells precipitated by centrifuging were dispersed in RPMI 1640 culture medium (made by Nissui Pharmaceutical Co., Ltd.) containing 10% bovine fetus serum or not containing 10% bovine fetus serum respectively. To each of the culture dishes, 1.5 ml of the culture medium containing $1 \times 10^6$ cells of macrophage was added and incubated at 37° C. under 5% $CO_2$ gaseous phase. After incubation, the culture dishes were washed with culture medium and the numbers of not adhered macrophages were counted and the numbers of the adhered macrophages were calculated by subtracting from all numbers of the inoculated cells.

Figure 4:
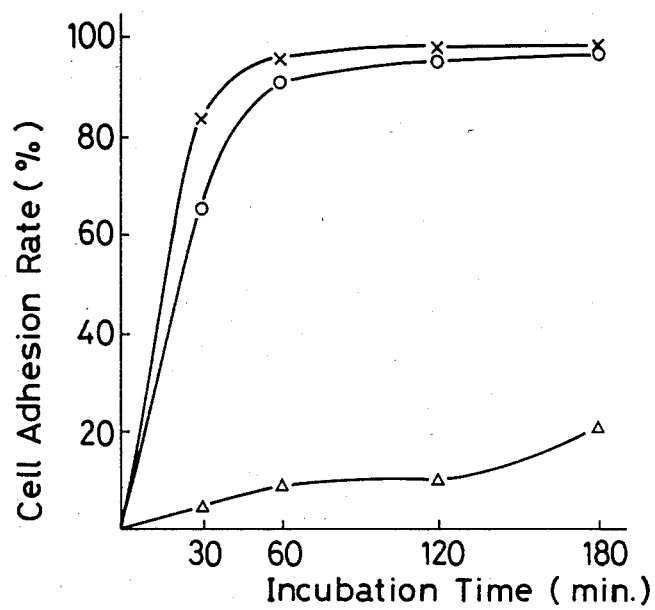
FIG. 4 is a graph showing the relation between the incubation time and the cell adhesion rate of macrophages by using various collagen substrates in the presence of bovine fetus serum.
Figure 5:
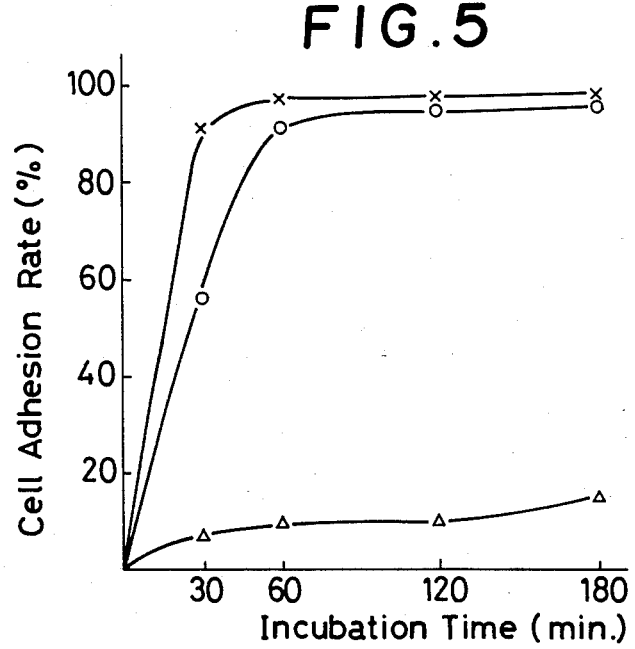
FIG. 5 is a graph showing the relation similar to FIG. 4 in the absence of bovine fetus serum.

The relation between the incubation time and adhesion rate of macrophage is shown in FIG. 4 and FIG. 5. FIG. 4 shows the result obtained in the presence of bovine fetus serum and FIG. 5 shows the result obtained in the absence of bovine fetus serum. In FIG. 4 and FIG. 5, the mark Δ represents the result obtained from unmodified atelocollagen, the mark 0 represents the result obtained from succinylated atelocollagen the mark x represents the result obtained from methylated atelocollagen.

As it is clear from FIG. 4 and FIG. 5, macrophage could adhere to succinylated collagen or methylated collagen in the presence of bovine fetus serum or even in the absence of bovine fetus serum at a high rate, and when incubated for longer than 60 minutes, adhesion more than 90% was shown. To the contrary macrophages were hardly adhered to unmodified collagen.

The exudate of the abdomen used by Example 3 contained macrophages in about 50% of all the cells and lymphocytes in the remained 50%. As the lymphocytes were not adhered to chemically modified collagen, macrophages could be isolated completely from lymphocytes by recovering the adhered macrophages.

To succinylated atelocollagen, methylated atelocollagen and unmodified atelocollagen, the macrophages were adhered by incubating at 37° C. for 3 hours in the presence of 10% bovine fetus serum. 1.5 ml of phosphate buffer solution containing 0.5 m mole/l of EDTA was added to the culture dishes adhering macrophages and was kept at 37° C. for 10 minutes to detach macrophages and detached macrophages were recovered. The numbers of the recovered macrophages were counted, and the recovery rate of the macrophages and the purity of the recovered macrophages were calculated.

TABLE 1

| Substrates | Recovery rate of macrophages (%) | Purity of recovered macrophages (%) |
|---|---|---|
| Succinylated atelocollagen | 41 | 94 |
| Methyalted | 48 | 92 |

TABLE 1-continued

| Substrates | Recovery rate of macrophages (%) | Purity of recovered macrophages (%) |
|---|---|---|
| atelocollagen Unmodified atelocollagen | 3 | 88 |

As understood from Table 1, macrophages with higher purity were obtained in the case that succinylated or methylated atelocollagen was used as a substratum, and the recovered macrophages were not injured.

What is claimed is:

1. In a mammalian cell culture containing a substratum and nutrient medium, the improvement comprising a substratum composed of collagen which has been modified by chemical means to increase the charge of the collagen to a degree sufficient to enhance mammalian cell attachment.

2. The cell culture according to claim 1, wherein the collagen is modified by chemical means to increase the negative charge of the collagen to a degree sufficient to enhance mammalian cell attachment.

3. The cell culture according to claim 1, wherein the collagen is modified by chemical means to increase the positive charge of the collagen to a degree sufficient to enhance mammalian cell attachment.

4. The cell culture according to claim 2, wherein the chemically modified collagen is succinylated collagen.

5. The cell culture according to claim 3, wherein the chemically modified collagen is esterified collagen.

6. The cell culture according to claim 4, wherein the succinylated collagen is succinylated more than 20 mol% of total amino groups of collagen.

7. The cell culture according to claim 3, wherein the esterified collagen is esterified more than 20 mol% of total carboxyl groups of collagen.

8. An improved method for culturing and isolating mammalian cells wherein the cells are cultured under conventional culture conditions, according to the type of cell being cultured, and collagen is used as a substratum for attaching the cells during culturing, the improvement comprising:

adhering the mammalian cells to collagen which has been modified by chemical means to increase the charge of the collagen, and incubating the mammalian cells and treating the animal cells with bivalent cation chelating agent to isolate and recover the cells.

9. A method according to claim 8, wherein macrophages are incubated in the mixed system with lymphocytes and only macrophages are selectively isolated and recovered.

10. A method according to claim 8, wherein the bivalent catin chelating agent is EDTA or EGTA.

11. A method according to claim 8, wherein the adhesion and incubation of mammalian cells are carried out in the presence of bovine fetus serum or fibronectin.

* * * * *